United States Patent
Batra et al.

(10) Patent No.: US 11,654,428 B2
(45) Date of Patent: May 23, 2023

(54) METHODS, SYSTEMS AND APPARATUS FOR SEPARATING COMPONENTS OF A BIOLOGICAL SAMPLE

(71) Applicant: Vias Partners, LLC, Doylestown, PA (US)

(72) Inventors: Sanjay Batra, New Hope, PA (US); Elizabeth G. Cellucci, Doylestown, PA (US); Justin Joseph Batra, New Hope, PA (US); Jaya Krishna Rose Batra, New Hope, PA (US)

(73) Assignee: Vias Partners, LLC

( * ) Notice: Subject to any disclaimer, the term of this patent is extended or adjusted under 35 U.S.C. 154(b) by 0 days.

(21) Appl. No.: 17/721,586

(22) Filed: Apr. 15, 2022

(65) Prior Publication Data

US 2022/0258156 A1 Aug. 18, 2022

Related U.S. Application Data

(63) Continuation of application No. 17/424,871, filed as application No. PCT/US2020/014446 on Jan. 21, 2020.

(60) Provisional application No. 62/794,961, filed on Jan. 21, 2019.

(51) Int. Cl.
  *C12N 5/078* (2010.01)
  *B01L 3/00* (2006.01)
  *B04B 5/04* (2006.01)
  *A61K 35/16* (2015.01)
  (Continued)

(52) U.S. Cl.
  CPC .......... *B01L 3/50215* (2013.01); *A61K 35/16* (2013.01); *A61K 35/19* (2013.01); *B01D 17/0217* (2013.01); *B04B 5/0414* (2013.01); *C12N 5/0644* (2013.01); *B01L 2200/026* (2013.01); *B01L 2200/0652* (2013.01); *B01L 2300/042* (2013.01); *B01L 2300/046* (2013.01);
  (Continued)

(58) Field of Classification Search
  CPC .......... B01L 3/50215; B01L 2200/026; B01L 2400/0409; B04B 5/0414; C12N 5/0644; A61K 35/16; A61K 35/19; B01D 17/0217
  See application file for complete search history.

(56) References Cited

U.S. PATENT DOCUMENTS

| | | |
|---|---|---|
| 10,618 A | 3/1854 | Wright |
| 1,543,846 A | 6/1925 | Hansen |
| 2,796,558 A | 6/1957 | Koehler |

(Continued)

FOREIGN PATENT DOCUMENTS

| | | |
|---|---|---|
| CA | 2181462 C | 8/2002 |
| CH | 696752 A5 | 11/2007 |

(Continued)

OTHER PUBLICATIONS

Abuzeni, P.Z., et al., "Enhancement of Autologous Fat Transplantation with Platelet Rich Plasma", The American Journal of Cosmetic Surgery vol. 18, No. 2, 2001, 12 pgs.

(Continued)

*Primary Examiner* — Marcia S Noble
*Assistant Examiner* — Lauren K Van Buren
(74) *Attorney, Agent, or Firm* — The Belles Group, P.C.

(57) ABSTRACT

Described herein are methods, systems and apparatus for separating components of a biological sample; as well as methods of using compositions prepared by same.

25 Claims, 9 Drawing Sheets

(51) Int. Cl.
  *A61K 35/19* (2015.01)
  *B01D 17/02* (2006.01)
(52) U.S. Cl.
  CPC .............. *B01L 2300/0832* (2013.01); *B01L 2400/0409* (2013.01)

(56) References Cited

U.S. PATENT DOCUMENTS

| | | |
|---|---|---|
| 3,774,454 A | 11/1973 | Shaw |
| 3,814,248 A | 6/1974 | Lawhead |
| 3,852,194 A | 12/1974 | Zine |
| 3,909,419 A | 9/1975 | Ayres |
| 3,929,646 A | 12/1975 | Adler |
| 3,957,654 A | 5/1976 | Ayres |
| 3,981,804 A | 9/1976 | Gigliello |
| 4,055,501 A | 10/1977 | Cornell |
| 4,101,422 A | 7/1978 | Lamont et al. |
| 4,148,764 A | 4/1979 | Lamont et al. |
| 4,190,535 A | 2/1980 | Luderer et al. |
| 4,267,269 A | 5/1981 | Grode et al. |
| 4,350,593 A | 9/1982 | Kessler |
| 4,567,754 A | 2/1986 | Wardlaw et al. |
| 4,599,219 A | 7/1986 | Cooper et al. |
| 4,752,449 A | 6/1988 | Jackson et al. |
| 4,784,990 A | 11/1988 | Nimrod et al. |
| 4,917,801 A | 4/1990 | Luderer et al. |
| 4,946,601 A | 8/1990 | Fiehler |
| 4,954,264 A | 9/1990 | Smith |
| 5,065,768 A | 11/1991 | Coleman et al. |
| 5,086,784 A | 2/1992 | Levine et al. |
| 5,174,961 A | 12/1992 | Smith |
| 5,236,604 A | 8/1993 | Fiehler |
| 5,252,557 A | 10/1993 | Kita et al. |
| 5,393,674 A | 2/1995 | Levine et al. |
| 5,462,752 A | 10/1995 | Chao et al. |
| 5,494,590 A | 2/1996 | Smith et al. |
| 5,510,102 A | 4/1996 | Cochrum |
| 5,510,237 A | 4/1996 | Isogawa et al. |
| 5,560,830 A | 10/1996 | Coleman et al. |
| 5,583,114 A | 12/1996 | Barrows et al. |
| 5,585,007 A | 12/1996 | Antanavich et al. |
| 5,589,167 A | 12/1996 | Cleland et al. |
| 5,667,963 A | 9/1997 | Smith et al. |
| 5,707,876 A | 1/1998 | Levine |
| 5,733,545 A | 3/1998 | Hood, III |
| 5,791,352 A | 8/1998 | Reich et al. |
| 5,891,617 A | 4/1999 | Watson et al. |
| 5,906,744 A | 5/1999 | Carroll et al. |
| 5,977,056 A | 11/1999 | Powell-Jones et al. |
| 6,054,122 A | 4/2000 | MacPhee et al. |
| 6,071,422 A | 6/2000 | Hlavinka et al. |
| 6,117,425 A | 9/2000 | MacPhee et al. |
| 6,123,655 A | 9/2000 | Fell |
| 6,197,325 B1 | 3/2001 | MacPhee et al. |
| 6,390,966 B2 | 5/2002 | Anderson |
| 6,398,972 B1 | 6/2002 | Blasetti et al. |
| 6,428,527 B1 | 8/2002 | Jones et al. |
| 6,465,256 B1 | 10/2002 | Iskra |
| 6,472,162 B1 | 10/2002 | Coelho et al. |
| 6,559,119 B1 | 5/2003 | Burgess et al. |
| 7,074,577 B2 | 7/2006 | Haubert et al. |
| 7,077,273 B2 | 7/2006 | Ellsworth et al. |
| 7,094,464 B2 | 8/2006 | Mao et al. |
| 7,112,342 B2 | 9/2006 | Worden |
| 7,153,477 B2 | 12/2006 | Dicesare et al. |
| 7,179,391 B2 | 2/2007 | Leach et al. |
| 7,223,346 B2 | 5/2007 | Dorian et al. |
| 7,329,534 B2 | 2/2008 | Haubert et al. |
| 7,358,095 B2 | 4/2008 | Haubert et al. |
| 7,374,678 B2 | 5/2008 | Leach et al. |
| 7,445,125 B2 | 11/2008 | Ellsworth et al. |
| 7,470,371 B2 | 12/2008 | Dorian et al. |
| 7,771,590 B2 | 8/2010 | Leach et al. |
| 7,780,860 B2 | 8/2010 | Higgins et al. |
| 7,837,884 B2 | 11/2010 | Dorian et al. |
| 7,845,499 B2 | 12/2010 | Higgins et al. |
| 7,915,029 B2 | 3/2011 | Haubert et al. |
| 7,947,236 B2 | 5/2011 | Losada et al. |
| 7,992,725 B2 | 8/2011 | Leach et al. |
| 8,012,742 B2 | 9/2011 | Haubert et al. |
| 8,048,297 B2 | 11/2011 | Leach et al. |
| 8,048,321 B2 | 11/2011 | Leach et al. |
| 8,119,013 B2 | 2/2012 | Leach et al. |
| 8,177,072 B2 | 5/2012 | Chapman et al. |
| 8,187,477 B2 | 5/2012 | Dorian et al. |
| 8,236,258 B2 | 8/2012 | Leach et al. |
| 8,282,839 B2 | 10/2012 | Ellsworth |
| 8,328,024 B2 | 12/2012 | Leach et al. |
| 8,348,066 B2 | 1/2013 | Ellsworth |
| 8,377,395 B2 | 2/2013 | Coleman |
| 8,394,342 B2 | 3/2013 | Felix et al. |
| 8,445,264 B2 | 5/2013 | Seubert et al. |
| 8,474,630 B2 | 7/2013 | Dorian et al. |
| 8,506,823 B2 | 8/2013 | Chapman et al. |
| 8,511,479 B2 | 8/2013 | Chapman et al. |
| 8,511,480 B2 | 8/2013 | Chapman et al. |
| 8,518,272 B2 | 8/2013 | Hoeppner |
| 8,529,957 B2 | 9/2013 | Turzi et al. |
| 8,596,470 B2 | 12/2013 | Leach et al. |
| 8,603,345 B2 | 12/2013 | Ross et al. |
| 8,603,346 B2 | 12/2013 | Leach et al. |
| 8,632,736 B2 | 1/2014 | Spatafore et al. |
| 8,632,740 B2 | 1/2014 | Dastane et al. |
| 8,747,781 B2 | 6/2014 | Bartfeld et al. |
| 8,794,452 B2 | 8/2014 | Crawford et al. |
| 8,808,551 B2 | 8/2014 | Leach et al. |
| 8,945,537 B2 | 2/2015 | Turzi |
| 8,950,586 B2 | 2/2015 | Dorian et al. |
| 8,992,862 B2 | 3/2015 | Leach et al. |
| 8,998,000 B2 | 4/2015 | Crawford et al. |
| 9,011,800 B2 | 4/2015 | Leach et al. |
| 9,079,123 B2 | 7/2015 | Crawford et al. |
| 9,095,849 B2 | 8/2015 | Losada et al. |
| 9,114,334 B2 | 8/2015 | Leach et al. |
| 9,120,095 B2 | 9/2015 | O'Connell |
| 9,138,664 B2 | 9/2015 | Leach et al. |
| 9,162,232 B2 | 10/2015 | Ellsworth |
| 9,239,276 B2 | 1/2016 | Landrigan et al. |
| 9,272,083 B2 | 3/2016 | Duffy et al. |
| 9,333,445 B2 | 5/2016 | Battles et al. |
| 9,339,741 B2 | 5/2016 | Newby et al. |
| 9,364,828 B2 | 6/2016 | Crawford et al. |
| 9,375,661 B2 | 6/2016 | Chapman et al. |
| 9,393,575 B2 | 7/2016 | Ellsworth et al. |
| 9,393,576 B2 | 7/2016 | Ellsworth et al. |
| 9,399,226 B2 | 7/2016 | Ellsworth et al. |
| 9,452,427 B2 | 9/2016 | Felix et al. |
| 9,517,255 B2 | 12/2016 | Turzi |
| 9,642,956 B2 | 5/2017 | Landrigan et al. |
| 9,656,274 B2 | 5/2017 | Ellsworth et al. |
| 9,694,359 B2 | 7/2017 | Losada et al. |
| 9,700,886 B2 | 7/2017 | Felix et al. |
| 9,714,890 B2 | 7/2017 | Newby et al. |
| 9,731,290 B2 | 8/2017 | Crawford et al. |
| 9,802,189 B2 | 10/2017 | Crawford et al. |
| 9,833,478 B2 | 12/2017 | Turzi et al. |
| 9,897,589 B2 | 2/2018 | Woodell-May |
| 9,919,307 B2 | 3/2018 | Crawford et al. |
| 9,919,308 B2 | 3/2018 | Crawford et al. |
| 9,919,309 B2 | 3/2018 | Crawford et al. |
| 9,933,344 B2 | 4/2018 | Newby et al. |
| 9,937,445 B2 | 4/2018 | King et al. |
| 10,005,081 B2 | 6/2018 | Duffy et al. |
| 10,052,349 B2 | 8/2018 | Turzi et al. |
| 10,092,598 B2 | 10/2018 | Turzi et al. |
| 10,183,042 B2 | 1/2019 | Leach et al. |
| 10,343,157 B2 | 7/2019 | Crawford et al. |
| 10,350,591 B2 | 7/2019 | Felix et al. |
| 10,376,879 B2 | 8/2019 | Crawford et al. |
| 10,393,728 B2 | 8/2019 | Woodell-May |
| 10,413,898 B2 | 9/2019 | Crawford et al. |
| 10,456,782 B2 | 10/2019 | Crawford et al. |
| 10,603,665 B2 | 3/2020 | Levine et al. |
| 10,618,044 B1 | 4/2020 | Petrie, Jr. |

(56) References Cited

U.S. PATENT DOCUMENTS

| | | |
|---|---|---|
| 2002/0123140 A1 | 9/2002 | Bandyopadhyay et al. |
| 2002/0187130 A1 | 12/2002 | Kindness et al. |
| 2002/0193448 A1 | 12/2002 | Wallace et al. |
| 2003/0161938 A1 | 8/2003 | Johnson |
| 2003/0205538 A1 | 11/2003 | Dorian et al. |
| 2003/0233064 A1 | 12/2003 | Arm et al. |
| 2004/0059255 A1 | 3/2004 | Manoussakis et al. |
| 2004/0071786 A1 | 4/2004 | Grippi et al. |
| 2004/0103951 A1 | 6/2004 | Osborne et al. |
| 2004/0151709 A1 | 8/2004 | Barrueta et al. |
| 2004/0208786 A1 | 10/2004 | Kevy et al. |
| 2004/0251217 A1 | 12/2004 | Leach et al. |
| 2005/0008629 A1 | 1/2005 | Arm |
| 2005/0170327 A1 | 8/2005 | Sumida et al. |
| 2005/0205498 A1 | 9/2005 | Sowemimo-Coker et al. |
| 2006/0128016 A1 | 6/2006 | Tokushima et al. |
| 2007/0034579 A1 | 2/2007 | Dorian et al. |
| 2007/0036766 A1 | 2/2007 | Kevy et al. |
| 2007/0184029 A1 | 8/2007 | Mishra |
| 2008/0089918 A1 | 4/2008 | Lebreton |
| 2008/0199845 A1 | 8/2008 | Rosiello et al. |
| 2009/0035382 A1 | 2/2009 | Aldecoa et al. |
| 2009/0274627 A1 | 11/2009 | Yamada et al. |
| 2009/0298173 A1 | 12/2009 | Ueda et al. |
| 2010/0015226 A1 | 1/2010 | Turzi et al. |
| 2010/0184720 A1 | 7/2010 | Molliard et al. |
| 2013/0058906 A1 | 3/2013 | Turzi |
| 2014/0010857 A1 | 1/2014 | Turzi et al. |
| 2015/0090650 A1 | 4/2015 | Grippi et al. |
| 2015/0151858 A1 | 6/2015 | Turzi |
| 2015/0231626 A1 | 8/2015 | Shi et al. |
| 2016/0158286 A1 | 6/2016 | Turzi et al. |
| 2017/0080028 A1 | 3/2017 | Turzi et al. |
| 2017/0087228 A1 | 3/2017 | Turzi |
| 2017/0258839 A1 | 9/2017 | Turzi et al. |
| 2017/0304823 A1 | 10/2017 | Sparks et al. |
| 2017/0326544 A1 | 11/2017 | Emerson |
| 2018/0296748 A1* | 10/2018 | Emerson ............... A61J 1/2013 |
| 2018/0304251 A1 | 10/2018 | Ellson et al. |
| 2018/0353952 A1 | 12/2018 | Olson |
| 2020/0009304 A1 | 1/2020 | Dorian et al. |
| 2020/0009552 A1 | 1/2020 | Crawford et al. |
| 2020/0129560 A1 | 4/2020 | Centeno et al. |
| 2020/0197929 A1 | 6/2020 | Weinstock et al. |
| 2020/0215243 A1 | 7/2020 | Dorian et al. |
| 2020/0246516 A1 | 8/2020 | Dorian et al. |
| 2020/0289720 A1 | 9/2020 | Streit |

FOREIGN PATENT DOCUMENTS

| | | |
|---|---|---|
| CN | 2623169 Y | 7/2004 |
| DE | 8910591 U1 | 12/1989 |
| EP | 0744026 B1 | 11/2001 |
| EP | 1547606 A1 | 6/2005 |
| EP | 1444984 B1 | 9/2008 |
| EP | 2068268 A1 | 6/2009 |
| EP | 2073862 A2 | 7/2009 |
| EP | 1543846 B1 | 8/2009 |
| EP | 2185163 A2 | 5/2010 |
| EP | 2544697 B1 | 5/2017 |
| EP | 31111974 A3 | 5/2017 |
| EP | 3184114 B1 | 10/2018 |
| ES | 2333498 B1 | 1/2011 |
| FR | 2918276 B1 | 1/2010 |
| JP | 2006515853 A | 6/2006 |
| JP | 2006181365 A | 7/2006 |
| JP | 2008214771 A | 9/2008 |
| JP | 2009235004 A | 10/2009 |
| JP | 2010535188 A | 11/2010 |
| JP | 2015232028 A | 12/2015 |
| KR | 20100075827 A | 7/2010 |
| RU | 2010107463 A | 9/2011 |
| WO | WO-8605984 A1 | 10/1986 |
| WO | WO-9515352 A1 | 6/1995 |
| WO | WO-9717025 A1 | 5/1997 |
| WO | WO-98/56247 A1 | 12/1998 |
| WO | WO-9966923 A1 | 12/1999 |
| WO | WO-9966964 A1 | 12/1999 |
| WO | WO-2000044022 A1 | 7/2000 |
| WO | WO-03092894 A2 | 11/2003 |
| WO | WO-2004024198 | 6/2004 |
| WO | WO-2004084825 A2 | 10/2004 |
| WO | WO-2005048958 A1 | 6/2005 |
| WO | WO-2006082661 A1 | 8/2006 |
| WO | WO-2006123579 A1 | 11/2006 |
| WO | WO-2006136870 A1 | 12/2006 |
| WO | WO-2008022651 A1 | 2/2008 |
| WO | WO-2008023026 A2 | 2/2008 |
| WO | WO-2009066102 A1 | 5/2009 |
| WO | WO-2009071445 A1 | 6/2009 |
| WO | WO-2009016451 A9 | 4/2010 |
| WO | WO-2009098698 A3 | 4/2010 |
| WO | WO-2011110948 A2 | 9/2011 |
| WO | WO-2012103100 A1 | 8/2012 |
| WO | WO-2012118922 A3 | 12/2012 |
| WO | WO-2013061309 A2 | 5/2013 |
| WO | WO-2016083549 A3 | 7/2016 |
| WO | WO-2018197562 A1 | 11/2018 |
| WO | WO-2018197564 A1 | 11/2018 |
| WO | WO-2018197592 A1 | 11/2018 |
| WO | WO-2019107509 A1 | 6/2019 |
| WO | WO-2020013981 A1 | 1/2020 |
| WO | WO-2020013997 A1 | 1/2020 |
| WO | WO-2020154305 A1 | 7/2020 |
| WO | WO-2020163105 A1 | 8/2020 |

OTHER PUBLICATIONS

Agrawal A.A., "Evolution, Current Status and Advances in Application of Platelet Concentrate in Periodontics and Implantology", World Journal of Clinical Cases May 16, 2017; 5(5): 159-171, ISSN 2307-8960 (online).

Alberts B., et al. "Molecular Biology of the Cell", 4th edition. New York: Garland Science; 2002. Chapter 19, "Cell Junctions, Cell Adhesion, and the Extracellular Matrix", 65 pgs.

Alberts B., et al. "Molecular Biology of the Cell", 6th edition. New York: Garland Science; 2008. Chapter 19, "Cell Junctions and the Extracellular Matrix", 29 pgs.

Annunziata M., et al, "In Vitro Cell-Types Specific Biological Response of Human Periodontally Related Cells to Platelet-Rich Plasma", Journal of Periodontal Research, 2005; 40; 489-495, 7 pgs.

Antoine Turzi & Regen Lab Team Biobridge Foundation Editions, Platelet-Rich Plasma (PRP) Standardization & Cell Therapies, Biobridge Foundation ed. www.briobridgeevent.com/knowledge, Regen Lab SA, www.regenlab.com, 180 pgs.

Appel, T.R., et al, "Comparison of Three Different Preparations of Platelet Concentrates for Growth Factor Enrichment", Clin. Oral Impl. Res. 13, 2002 I 522-528, 7 pgs.

BD Vacutainer CPT Cell Preparation Tube with Sodium Citrate. Product Insert, 2003.

Becton Dickinson Vacutainer Tube Guide, 2005.

Biomet Biologies, Recover Platelet Separation Kit, 20 pgs.

Biomet Europe, Cell Factor Technologies, Inc., GPS II System, Gravitational Platelet Separation System User Manual, 14 pgs.

Bornes, T.D., et al, "Mesenchymal Stem Cells in the Treatment of Traumatic Articular Cartilage Defects: A Comprehensive Review", Arthritis Research & Therapy 2014; 16(5), 30 pgs.

Braccini, F., et al, "Platelet-Rich Fibrin during Facial Lipostructure" Body Language, The UK Journal of Medical Aesthetics and Anti-Ageing, pp. 51-54.

Castillo, T. N., et al, "Comparison of Growth Factor and Platelet Concentration from Commercial Platelet-Rich Plasma Separation Systems", The American Journal of Sports Medicine, Feb. 2011;39(2):266-271.

Cellenis PRP Revive Your Natural Beauty in a Natural Way, Estar Aesthetics, www.estar-medical.com, 2 pgs. Tropocells System.

Cellenis PRP Skin Rejuvenation, PRP Preparation Simplicity For Success, 2 pgs., www.estar-medical.com, Tropocells System.

(56) References Cited

OTHER PUBLICATIONS

Celotti, F.,et al., "Effect of platelet-rich plasma on migration and proliferation of SaOS-2 osteoblasts: role of platelet-derived growth factor and transforming growth factor," Wound Repair and Regeneration (2006) 14; 195-202.
Christensen, K., et al, "Autologous Platelet Gel: An In Vitro Analysis of Platelet-Rich Plasma Using Multiple Cycles", The Journal of The American Society of Extra-Corporeal Technology, 2006; 38:249-253.
Claim Chart for U.S. Appl. No. 12/438,236.
Currie, L.J., et al, "The Use of Fibrin Glue in Skin Grafts and Tissue-Engineered Skin Replacements: A Review" Plastic and Reconstructive Surgery, Nov. 2001 , vol. 108, No. 6, 1713-1726.
de Oliveira S, Saldanha C., An overview about erythrocyte membrane. Clin Hemorheol Microcirc. 2010; 44(1):63-74.
Delong, J.M., et al., "Level V. Evidence, Platelet-Rich Plasma: The PAW Classification System", Arthroscopy: The Journal of Arthroscopic and Related Surgery, vol. 28, No. 7 Jul. 2012: pp. 998-1009.
Demiralp, B., et al, "Treatment of Periapical Inflammatory Lesion with the Combination of Platelet-Rich Plasma and Tricalcium Phosphate: A Case Report", The American Association of Endodontists, Journal of Endodontics vol. 30, No. 11, Nov. 2004; pp. 796-800.
Details of clinical trial NCT00856934 from CliniciaiTrials.gov. Effect of Platelet Rich Plasma and Keratinocyte Suspensions on Wound Healing, 19 pgs.
Doucet, C., et al. "Platelet Lysates Promote Mesenchymal Stem Cell Expansion: A Safety Substitute for Animal Serum in Cell-Based Therapy Applications," Journal of Cellular Physiology 205: 228-236 (2005).
Eppley B.L., et al, "Platelet quantification and growth factor analysis from platelet-rich plasma: implications for wound healing", American Society of Plastic Surgeons Nov. 2004; 114(6):1502-1508.
Eppley, B.L, et al, "Platelet-Rich Plasma: A Review of Biology and Applications in Plastic Surgery", Plastic and Reconstructive, Nov. 2006, vol. 118, No. 6, pp. 147e-159e.
Everts et al., "Platelet rich plasma and platelet gel, A review." J. Extra Corpor. Techn. 2006; 38: 174-187. Presented at: 21st Mechanisms of Perfusion Congress, May 18-21, 2006, Orlando FL, USA.
Everts, P.A., et al, "Platelet-rich plasma preparation using three devices: Implications for platelet activation and platelet growth factor release" Growth Factors, Sep. 2006; 24(3 ): 165-171.
Evidence Based Healthcare Group, "Efficacy of Autologous Platelet Rich Plasma in Bone Healing—Evidence Based Review", Jun. 2007, pp. 1-32.
Ferreira C.F., et al, "Platelet-rich plasma influence on human osteoblasts growth", Clinical Oral Implants Research, Aug. 2005;16(4):456-460.
Forni, F., et al, "Platelet gel: applications in dental regenerative surgery", Blood Transfus. Jan. 2013;1 1(1):102-107.
Fried, D.W., et al., Quantitative and qualitative analysis of plateletrich plasma collection using the Haemonetics Cell Saver 5 in open heart surgery, The Journal of The American Society of Extra-Corporeal Technology, Sep. 2006;38(3):235-240.
Fulton, J. "Breast Contouring with 'Gelled' Autologous Fat: A 10-Year Update" International Journal of Cosmetic Surgery and Aesthetic Dermatology, 2003, pp. 155-163, vol. 5, No. 2.
Gadol et al., "A new method for separating mononuclear cell from whole blood," Diagn. lmmunol. 1985; 3(3): 145-154.
Garratty, G., Teien, M.J., Petz. L.D., "Red cell antigens as functional molecules and obstacles to transfusion", Hematology Am Soc Hematol Educ Progre 鄂 n. 2002:445-462.
Gentile, P., Di Pasquali, C., Bocchini, I., Floris, M., Eleonora. T., Fiaschetti. V., Floris. R., Cervelli. V., Breast reconstruction with autologous fat graft mixed with platelet-rich plasma. Surg Innov. Aug. 2013; 20(4):370-376.
Gluckman, E, Rocha, V, Boyer-Chammard, A, Locatelli, F, Arcese, W, Pasquini, R, Ortega, J, Souillet G, Ferreira E, Laporte, JP, Fernandez, M., Chastang, C., Outcome of cordblood transplantation from related and unrelated donors. Eurocord Transplant Group and the European Blood and Marrow Transplantation Group. N Engl J Med. Aug. 7, 1997;337(6):373-381.
Gobbi, A, Karnatzikos, G, Mahajan, V, Malchira, S., Platelet rich plasma treatment in symptomatic patients with knee osteoarthritis: preliminary results in a group of active patients. Sports Health. Mar. 2012;4(2):162-172.
Graziani et al., "The in vitro effect of different PRP concentrations on osteoblasts and fibroblasts", Clinical Oral. Implants Research May 2006; 17(2): 212-219.
Greco, J., "Micro Needling and Injecting Platelet Rich Plasma to Enhance Collagen Synthesis and Skin Tightening." (2007).
Greiner Bio-One, Instructions on Proper Use of Serum Tubes, 2 pgs.
Guerid, S., Darwiche, SE, Berger, MM, Applegate, LA, Benathan, M., Raffoul, W., Autologous keratinocyte suspension in platelet concentrate accelerates and enhances wound healing—a prospective randomized clinical trial on skin graft donor sites: platelet concentrate and keratinocytes on donor sites. Fibrogenesis Tissue Repair. Apr. 9, 2013;6(1):8.
Guy Fortier et al., "Study Report, Regen THT Tube Performance Testing at US FDA Request", Study 2010-01 REV00, 2010, 17 pgs.
Hanson, SR, Harker, LA., Interruption of acute plateletdependent thrombosis by the synthetic antithrombin D-phenylalanyl-L-prolyl-L-arginyl chloromethyl ketone. Proc Natl Acad Sci USA. May 1988;85(9):3184-3188.
Haynesworth, S. et al. "Mitogenic Stimulation of Human Mesenchymal Stem Cells by Platelet Releasate Suggests a Mechanism for Enhancement of Bone Repair by Platelet Concentrate." 48th Annual Meeting of the Orthopaedic Research Society, Poster No. 0462 (2001).
Hooiveld, MJ, Roosendaal, G., van den Berg, HM, Bijlsma, JW, Lafeber, FP., Haemoglobin-derived iron-dependent hydroxyl radical formation in blood-induced joint damage: an in vitro study. Rheumatology (Oxford). Jun. 2003;42(6):784-790. Epub Mar. 31, 2003.
Kaux, JF, Le Goff, C., Renouf, J., Peters, P., Lutteri, L., Gothot, A., Crielaard, JM., Comparison of the platelet concentrations obtained in platelet-rich plasma (PRP) between the GPS™ II and GPS™ III systems. Pathol Biol (Paris). Oct. 2011;59(5):275-277. Epub Dec. 8, 2010.
Kaux, JF, Le Goff, C., Seidel, L., Peters, P., Gothot, A., Albert, A., Crielaard. JM., Etude comparative de cinq techniques de preparation plaquettaire (platelet-rich plasma) [Comparative study of five techniques of preparation of platelet-rich plasma]. Pathol Biol (Paris). Jun. 2011;59(3):157-60. French. Epub May 28, 2009.
Kawase, T., Okuda, K., Wolff, LF, Yoshie. H., Platelet-rich plasma-derived fibrin clot formation stimulates collagen synthesis in periodontal ligament and osteoblastic cells in vitro. J Periodontol. Jun. 2003;74(6):858-864.
Kevy, SV, Jacobson, MS., Comparison of methods for point of care preparation of autologous platelet gel. J Extra Corpor Technol. Mar. 2004; 36(1):28-35.
Kubota, S, Kawata, K, Yanagita, T, Doi, H, Kitoh, T, Takigawa, M., Abundant retention and release of connective tissue growth factor (CTGF/CCN2) by platelets. J Biochem. Sep. 2004; 136(3):279-282.
Kubota Y, Tanaka T, Ohnishi H, Kitanaka A, Okutani Y, Taminato T, Ishida T, Kamano H. Constitutively activated phosphatidylinositol 3-kinase primes platelets from patients with chronic myelogenous leukemia for thrombopoietin-induced aggregation. Leukemia. Jun. 2004;18(6):1127-1137.
Kushida S, Kakudo N, Morimoto N, Hara T, Ogawa T, Mitsui T, Kusumoto K. Platelet and growth factor concentrations in activated platelet-rich plasma: a comparison of seven commercial sep 肛 ation systems. J ArtifOrgans. Jun. 2014;1 7(2):186-92. Epub Apr. 20, 2014.
Landi A, Tarantino R, Marotta N, Ruggeri AG, Domenicucci M, Giudice L, Martini S, Rastelli M, Ferrazza G, De Luca N, Tomei G, Delfini R. The use of platelet gel in postero-lateral fusion: preliminary results in a series of 14 cases. Eur Spine J. May 2011;20 Suppl 1(Suppl 1):S61-7. Epub Mar. 17, 2011. PMID: 21416280.
Laurens, I. "Development of a new extraction method for platelet-rich plasma and partial purification of plateletderived growth factor and transforming growth factor beta" University of Pretoria, Oct. 2013, pp. 148.
Leitner GC, Gruber R, Neumilller J, Wagner A, Kloimstein P, Hocker P, Kormoczi GF, Buchta C. Platelet content and growth

(56) References Cited

OTHER PUBLICATIONS factor release in platelet-rich plasma: a comparison of four different systems. Vox Sang. Aug. 2006;91(2):135-139.
Lind M. Growth factors: possible new clinical tools. A review. Acta Orthop Scand. Aug. 1996;67(4):407-17.
Lippross, S. and M. Alini. "Platelet-rich plasma for bone healing—to use or not to use ?" (2007).
Liu L, Hartwig D, HarloffS, Herminghaus P, Wedel T, Kasper K, Geerling G. Corneal epitheliotrophic capacity of three different blood-derived preparations. Invest Ophthalmol Vis Sci. Jun. 2006;47(6):2438-44.
Liu Y, Kalen A, Risto O, Wahlstrom O., Fibroblast proliferation due to exposure to a platelet concentrate in vitro is pH dependent. Wound Repair Regen. Sep.-Oct. 2002; 10(5):336-40.
Lozada JL, Caplanis N, Proussaefs P, Willardsen J, Kammeyer G. Platelet-rich plasma application in sinus graft surgery: Part I—Background and processing techniques. J Oral lmplantol. 2001;27(1):38-42.
Magalon J, Bausset O, Serratrice N, Giraudo L, Aboudou H, Veran J, Magalon G, Dignat-Georges F, Sabatier F. Characterization and comparison of 5 platelet-rich plasma preparations in a single-donor model. Arthroscopy. May 2014;30(5):629-638.
Magalon J, Chateau AL, Bertrand B, Louis ML, Silvestre A, Giraudo L, Veran J, Sabatier F. DEPA classification: a proposal for standardising PRP use and a retrospective application of available devices. BMJ Open Sport Exerc Med. Feb. 4, 2016;2(1 ).
Maino VC, Suni MA, Ruitenberg JJ. Rapid flow cytometric method for measuring lymphocyte subset activation. Cytometry. Jun. 1, 1995;20(2):127-133.
Man D, Plosker H, Winland-Brown JE. The use of autologous platelet-rich plasma (platelet gel) and autologous platelet-poor plasma (fibrin glue) in cosmetic surgery. Plast Reconstr Surg. Jan. 2001;107(1):229-37; discussion 238-9.
Mandle, Robert, Research Study, Comparison of EmCyte GS30-PurePRP II, EmCyte GS60-PurePRP II, Arteriocyte Magellan, Stryker RegenKit THT, and Eclipse PRP, May 6, 2016, 14 pgs.
Marlovits S, Mousavi M, Gabler C, Erdos J, Vecsei V., A new simplified technique for producing platelet-rich plasma: a short technical note. Eur Spine J. Oct. 2004; 13 Suppl 1(Suppl 1):8102-6. Epub Jun. 22, 2004.
Martin Lind (1996) Growth factors: Possible new clinical tools: A review, Acta Orthopaedica Scandinavica, 67:4, 407-417.
Marx RE, Carlson ER, Eichstaedt RM, Schimmele SR, Strauss JE, Georgeff KR. Platelet-rich plasma: Growth factor enhancement for bone grafts. Oral Surg Oral Med Oral Pathol Oral Radiol Endod. Jun. 1998;85(6):638-46.
Marx RE. Platelet-rich plasma (PRP): what is PRP and what is not PRP? Implant Dent. 2001;10(4):225-8.
Mazzucco L, Medici D, Serra M, Fanizza R, Rivara G, Orecchia S, Libener R, Cattana E, Levis A, Betta PG, Borzini P. The use of autologous platelet gel to treat difficult-to-heal wounds: a pilot study. Transfusion. Jul. 2004;44(7): 1013-1018.
Mazzucco L., et al, Platelet-Rich Plasma and Platelet Gel Preparation Using Plateltex®, Journal Compilation 2008 Blackwell Publishing Ltd., Vor Sanquinis, 7 pgs.
Melmed EP. Autologous platelet gel in plastic surgery. Aesthet Surg J. Jul. 2001;21(4):377-9.
Mishra A, Harmon K, Woodall J, Vieira A. Sports medicine applications of platelet rich plasma. Curr Pharm Biotechnol. Jun. 2012;13(7):1185-95.
Mishra A, Pavelko T. Treatment of chronic elbow tendinosis with buffered platelet-rich plasma. Am J Sports Med. Nov. 2006;34(11):1774-8. Epub May 30, 2006.
Mizuno D, Kagami H, Mizuno H, Mase J, Usami K, Ueda M. Bone regeneration of dental implant dehiscence defects using a cultured periosteum membrane. Clin Oral Implants Res. Mar. 2008; 19(3):289-94. Epub Dec. 13, 2007.
Napolitano M, Matera S, Bossio M, Crescibene A, Costabile E, Almolla J, Almolla H, Togo F, Giannuzzi C, Guido G. Autologous platelet gel for tissue regeneration in degenerative disorders of the knee. Blood Transfus. Jan. 2012;10(1):72-7. Epub Oct. 25, 2011.
NCCLS. "Tubes and Additives for Venous Blood Specimen Collection; Approved Standard" Fifth Edition.NCCLS document H1-A5 [ISBN 1-56238-519-4]. NCCLS, 940 West Valley Road, Suite 1400, Wayne, Pennsylvania 19087-1898 USA, 2003.
Okuda K, Kawase T, Momose M, Murata M, Saito Y, Suzuki H, WolffLF, Yoshie H. Platelet-rich plasma contains high levels of platelet-derived growth factor and transforming growth factor-beta and modulates the proliferation of periodontally related cells in vitro. J Periodontol. Jun. 2003;74(6):849-57.
OMS Patient Procedures, Bone Grafting, Whitewater Oral Surgery Group, http://www.whitewatersurgery.com, 5 pgs.
Pape HC, Evans A, Kobbe P. Autologous bone graft: properties and techniques. J Orthop Trauma. Mar. 2010;24 Suppl 1 :S36-40.
Parkinson, E. K. et al., "3. The Epidermis""Culture of Epithelial Cells", 2002, pp. 65-94, 2nd Edition.
PCT Patent Application No. PCT/EP2006/065493 dated Aug. 21, 2006, Inventor Antoine Turzi, 35 pgs.
Perttila J, Salo M, Peltola O. Plasma fibronectin concentrations in blood products. Intensive Care Med. 1990; 16(1):41-3.
Pierce GF, Vande Berg J, Rudolph R, Tarpley J, Mustoe TA. Platelet-derived growth factor-BB and transforming growth factor beta 1 selectively modulate glycosaminoglycans, collagen, and myofibroblasts in excisional wounds. Am J Pathol. Mar. 1991;138(3):629-646.
Pietrzak WS, Eppley BL. Platelet rich plasma: biology and new technology. J Craniofac Surg. Nov. 2005;16(6):1043-1054.
Platelet count—definition of platelet count by medical dictionary, https://medicaldictionary.thefreedictionary.com/platelet+count.
Powell DM, Chang E, Farrior EH. Recovery from deepplane rhytidectomy following unilateral wound treatment with autologous platelet gel: a pilot study. Arch Facial Plast Surg. Oct.-Dec. 2001;3(4):245-50.
Raffoul, Wassim & Guerid, S. & Darwich, S. & Berger, Mette & Hayoz, Daniel & Benathan, M . . . (2008). Impact of platelets concentrate and keratinocyte suspension on wound healing—a prospective randomized trial. The International journal of artificial organs. 31. 16 pgs.
Regen Lab brochure entitled "RegenPRP-Kit" available at www.regenkit.com as of Sep. 26, 2004.
Regen Lab presentation entitled "Innovation in Biological Tissue Regeneration", 2005.
Rheinwald JG, Green H. Serial cultivation of strains of human epidermal keratinocytes: the formation of keratinizing colonies 台 om single cells. Cell. Nov. 1975;6(3):33 1-43.
Rheinwald, J. G. et al. "Formation of a Keratinizing Epithelium in Culture by a Cloned Cell Line Derived 企 om a Teratoma" Cell, Nov. 1975, pp. 317-330, vol. 6.
Ronfard, V. et al., "Use of Human Keratinocytes Cultured on Fibrin Glue in the Treatment of Burn Wounds," Burns, 1991, pp. 181-184, vol. 17, No. 3.
Sadati, K., et al, "Platelet-Rich Plasma (PRP) Utilized To Promote Greater Graft Volume Retention in Autologous Fat Grafting", The American Journal of Cosmetic Surgery, vol. 23, No. 4, 2006.
Sanchez AR, Sheridan PJ, Kupp LI. Is platelet-rich plasma the perfect enhancement factor? A current review. Int J Oral Maxillofac Implants. Jan.-Feb. 2003;18(1):93-103.
Sanchez M, Anitua E, Azofra J, Aguirre JJ, Andia I. Intraarticular injection of an autologous preparation rich in growth factors for the treatment of knee OA: a retrospective cohort study. Clin Exp Rheumatol. Sep.-Oct. 2008;26(5):9 1 0-3.
Schnabel L V, Mohammed HO, Miller BJ, McDermott WG, Jacobson MS, Santangelo KS, Fortier LA. Platelet rich plasma (PRP) enhances anabolic gene expression patterns in flexor digitorum superficialis tendons. J Orthop Res. Feb. 2007;25(2):230-40.
Selected Normal Pediatric Laboratory Values, https://pdf4pro.com/view/selected-normal-pediatriclaboratory-values-37fca4.html.
Shenkman B, Brill A, Brill G, Lider 0, Savion N, Varon D. Differential response of platelets to chemokines:RANTES non-competitively inhibits stimulatory effect of SDF-1 alpha. J Thromb Haemost. Jan. 2004;2(1):154-160.

(56) References Cited

OTHER PUBLICATIONS

Slater M, Patava J, Kingham K, Mason RS. Involvement of platelets in stimulating osteogenic activity. J Orthop Res. Sep. 1995; 13(5):655-63.

Slichter, et al., "Platelet Transfusion Therapy", Chapter 14 in "Platelets In Hematologic And Cardiovascular Disorders. A Clinical Handbook". Edited by Paolo Gresele et al.; Cambridge University Press 2008.

Smith, R. G. et al. "Platelet-rich Plasma: Properties and Clinical Applications." The Journal of Lancaster General Hospital • Summer 2007 • vol. 2—No. 2.

Sotiri I, Overton JC, Waterhouse A, Howell C. Immobilized liquid layers: A new approach to antiadhesion surfaces for medical applications. Exp Biol Med (Maywood). May 2016;241(9):909-18. Epub Mar. 27, 2016.

Storry, JR. Review: the function of blood group-specific RBC membrane components. Immunohematology. 2004;20(4):206-216.

Stryer, L. Biochemistry, 3rd Edition. Stanford University, W.H. Freeman & Company, New York, Chapter 11, Connective-Tissue Proteins.

The Merck Manual for Health Care Professionals, "Appendix II Normal Laboratory Values", 2011, RP• 1-9.

Thermo Scientific, Tech Tip #40, Convert Between Times Gravity (xg) and Centrifuge Rotor Speed (RPM), 1 pg.

Tischler M. "Platelet rich plasma—utilizing autologous growth factors for dental surgery to enhance bone and soft tissue grafts", New York State Dental Journal 3-02.

Toit, Don F & Kleintjes, Wayne & Otto, Morkel & Mazyala, Erick J & Page, Benedict J. Soft and hard-tissue augmentation with platelet-rich plasma: Tissue culture dynamics, regeneration and molecular biology perspective. International Journal of Shoulder Surgery. USS Apr. 2007, vol. 1, Issue 2.

Tozum TF, Demiralp B. Platelet-rich plasma: a promising innovation in dentistry. J Can Dent Assoc. Nov. 2003;69(10):664.

Tsay et al., "Differential growth factor retention by platelet-rich plasma composites". J. Oral. Maxil/ofac. Surg. 2005. 63: 521-528.

Van Den Dolder, J. et al.,"Platelet-Rich Plasma: Quantification of Growth Factor Levels and the Effect on Growth and Differentiation of Rat Bone Marrow Cells", Tissue Engineering, vol. 12, No. 11, 2006; pp. 3067-3073.

Van Laethem K, Beuselinck K, Van Dooren S, De Clercq E, Desmyter J, Vandamme AM. Diagnosis of human immunodeficiency virus infection by a polymerase chain reaction assay evaluated in p剖ients harbouring strains of diverse geographical origin. J Virol Methods. Feb. 1998;70(2): 153-66.

Wang HL, Avila G. Platelet rich plasma: myth or reality? Eur J Dent. Oct. 2007;1(4):192-4.

Waters JH, Roberts KC. Database review of possible factors influencing point-of-care platelet gel manufacture. J Extra Corpor Technol. Sep. 2004;36(3):250-4.

Weibr划1 G, Hansen T, Kleis W, Buch R, Hitzler WE. Effect of platelet concentration in platelet-rich plasma on peri-implant bone regeneration. Bone. Apr. 2004;34(4):665-71.

Weibrich G, Kleis WK, Buch R, Hitzler WE, Hafner G. The Harvest Smart PRePTM system versus the Friadent-Schiltze platelet-rich plasma kit. Clin Oral Implants Res. Apr. 2003; 14(2):233-9.

Weibrich G, Kleis WK. Curasan PRP kit vs. PCCS PRP system. Collection efficiency and platelet counts of two different methods for the preparation of platelet-rich plasma. Clin Oral Implants Res. Aug. 2002;13(4):437-43.

Weibrich G., et al, "Effect of Platelet Concentration in Platelet-Rich Plasma on Peri-Implant Bone Regeneration", Elsevier, Bone 34 (2004) 665-671.

Woodell-May JE, Ridderman DN, Swift MJ, Higgins J. Producing accurate platelet counts for platelet rich plasma: validation of a hematology analyzer and preparation techniques for counting. J Craniofac Surg. Sep. 2005;16(5):749-56; discussion 757-9.

World Health Organization, "Use of Anticoagulants in Diagnostic Laboratory Investigations", 2002 WHO/DIL/LAB/99.1Rev.2,64 pgs.

Wyss Institute for Biologically Inspired Engineering at Harvard. "Bioinspired coating for medical devices repels blood, bacteria." ScienceDaily. ScienceDaily, Oct. 12, 2014.

Zenker S., "Platelet Rich Plasma (PRP) for Facial Rejuven创on" J. Med. Esth. et Chir. Derm. vol. XXXVII, 148, Dec. 2010, 179-183.

Zillmann A, Luther T, Milller I, Kotzsch M, Spannagl M, Kauke T, Oelschlagel U, Zahler S, Engelmann B. Plateletassociated tissue factor contributes to the collagentriggered activation of blood coagulation. Biochem Biophys Res Commun. Feb. 23, 2001;281(2):603-9.

\* cited by examiner

METHODS, SYSTEMS AND APPARATUS FOR SEPARATING COMPONENTS OF A BIOLOGICAL SAMPLE

CROSS-REFERENCE TO RELATED APPLICATION

This application is a continuation of U.S. application Ser. No. 17/424,871 filed Jul. 21, 2021, which is a US 371 application from PCT/US2020/014446 filed Jan. 21, 2020, published as WO 2020/154305 on Jul. 30, 2020, which claims the benefit of priority from U.S. Provisional Application No. 62/794,961 filed Jan. 21, 2019; the contents of which are hereby incorporated herein in their entireties.

BACKGROUND

Platelet-rich plasma (PRP) is generally understood to be a concentrate of platelets and plasma, that also contains growth factors, such as Platelet-Derived Growth Factor (PDGF); Transforming Growth Factor group (TGF); Epidermal Growth Factor (EGF); Vascular Endothelial Growth Factor (VEGF); Fibroblast Growth Factor (FGF); and Keratinocyte Growth Factor (KGF), which regulate the healing cascade by signaling surrounding cells to repair damaged tissue and regenerate new tissue.

Various methods and systems for preparing PRP are known; but for a variety of reasons, these methods and systems do not consistently provide efficient platelet capture. For example, devices and systems utilizing a separator gel, tend to have issues with platelets adhering to the separator gel. As a result, the clinician is often left with a less than desirable number of platelets available for administration to a patient.

Thus, there remains a need for simple, cost-effective, reliable and clinically useful methods for overcoming the aforementioned challenges; and that enrich platelet concentrations and increase the number of platelets available for administration to a patient. Embodiments of the present invention are designed to meet these and other ends.

SUMMARY

In some embodiments, the claimed invention is directed to methods for separating components of a biological sample, the method comprising: introducing a biological sample having a plurality of components to a tube comprising: a lumen; a proximal end; a distal end; an interior wall; and an exterior wall; applying a force to said tube for a time sufficient to separate said plurality of components; and agitating said tube at an angle (e.g. from about 5° to about 60°) effective to enrich the concentration of a component of the biological sample (e.g. platelets).

Other embodiments provide compositions comprising a product produced by any one of the methods or systems described herein. While other embodiments provide methods of using a product produced by any one of the methods or systems described herein Still further embodiments provide system for separating components of a biological sample comprising: a biological sample; a tube; a means for applying a centrifugal force to said tube; and a means for agitating said tube.

DETAILED DESCRIPTION

Figure 1:
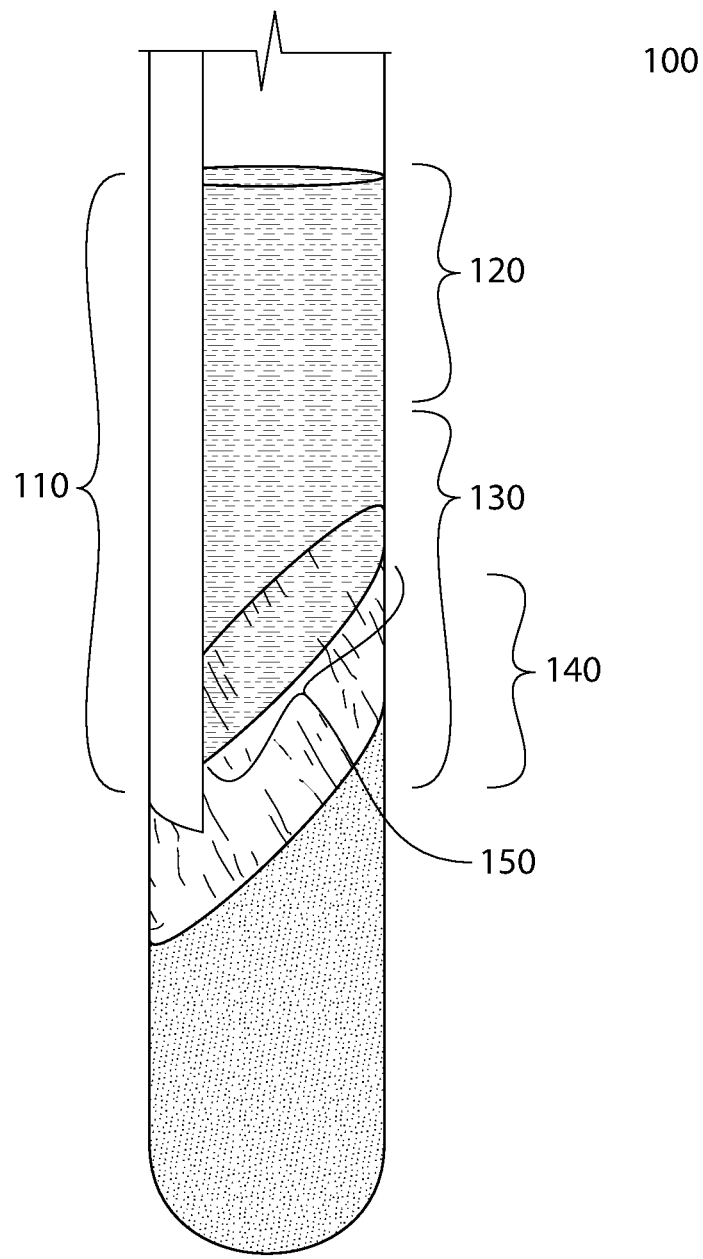
FIG. 1 depicts an exemplary tube of the present invention after centrifugation.
Figure 2:
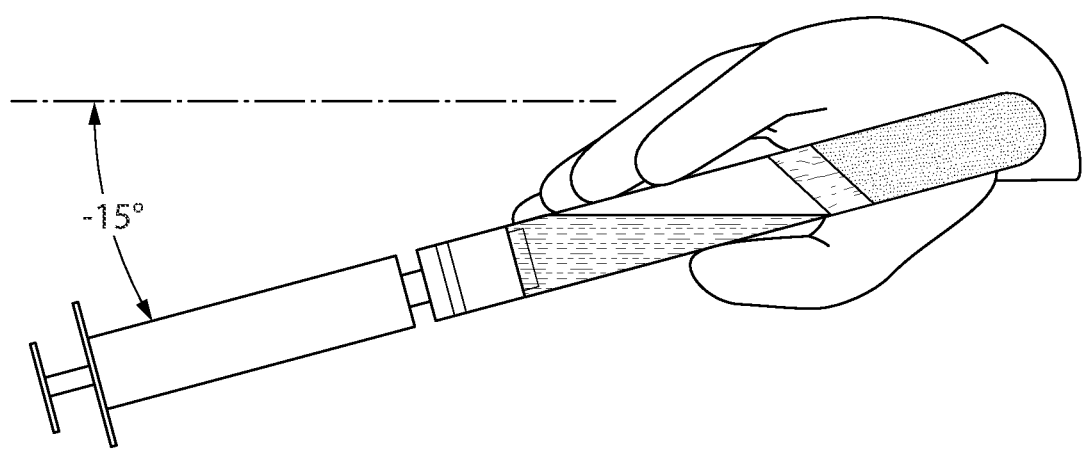
FIG. 2 depicts a first comparative agitation angle.
Figure 3:
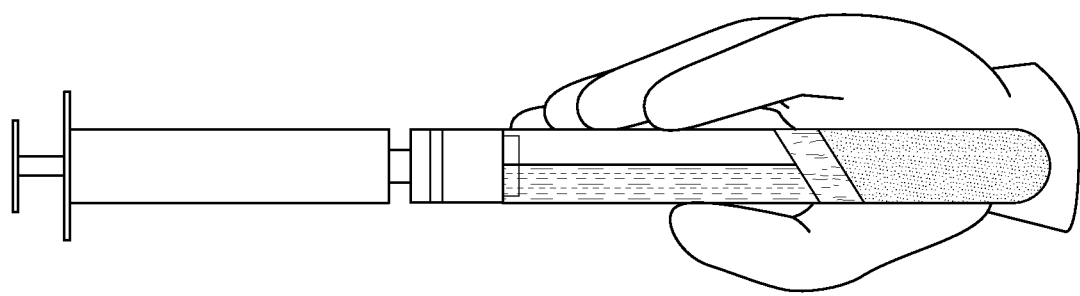
FIG. 3 depicts a second comparative agitation angle.
Figure 4:
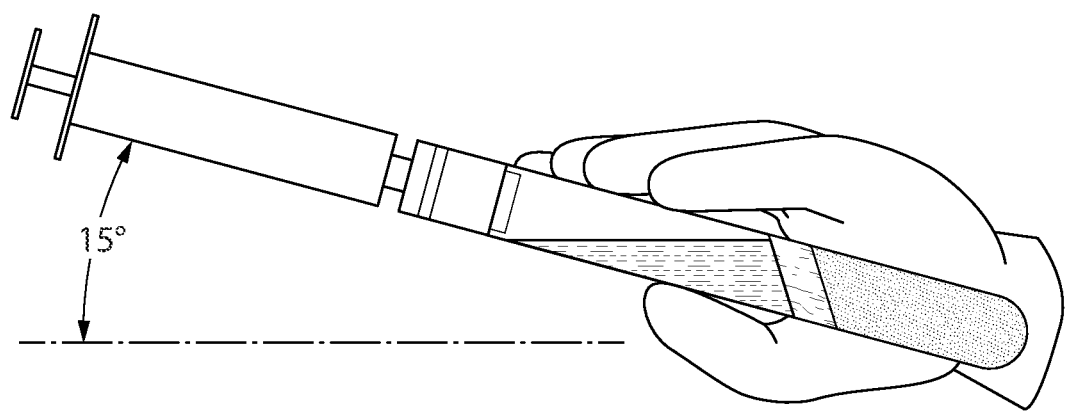
FIG. 4 depicts a first exemplary agitation angle according to certain embodiments of the present invention.
Figure 5:
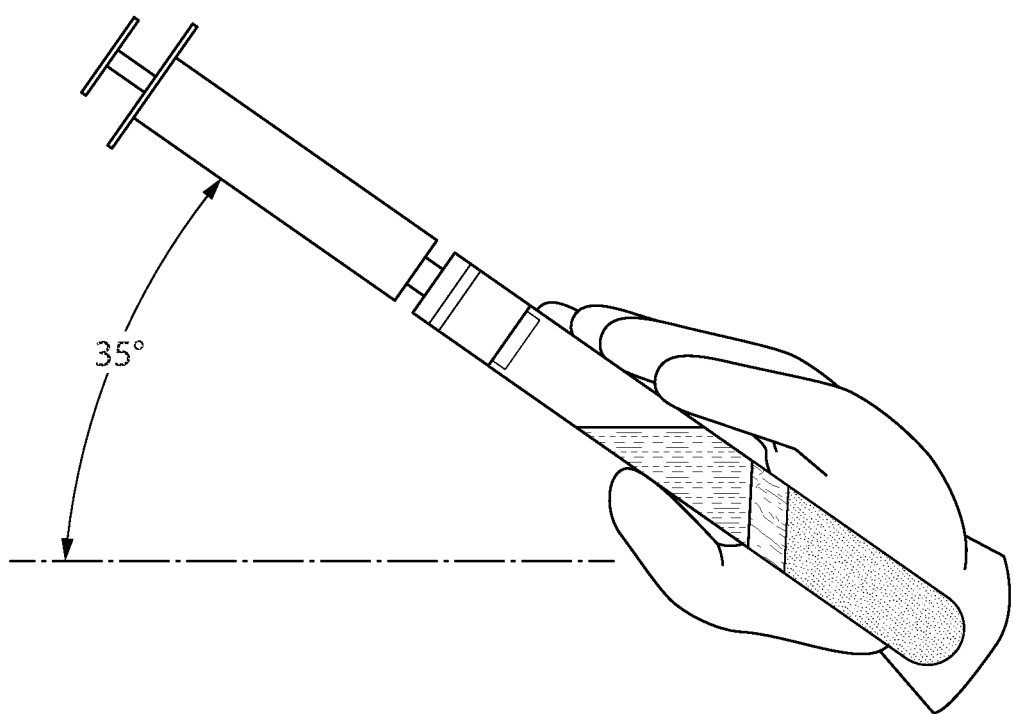
FIG. 5 depicts a second exemplary agitation angle according to certain embodiments of the present invention.
Figure 6:
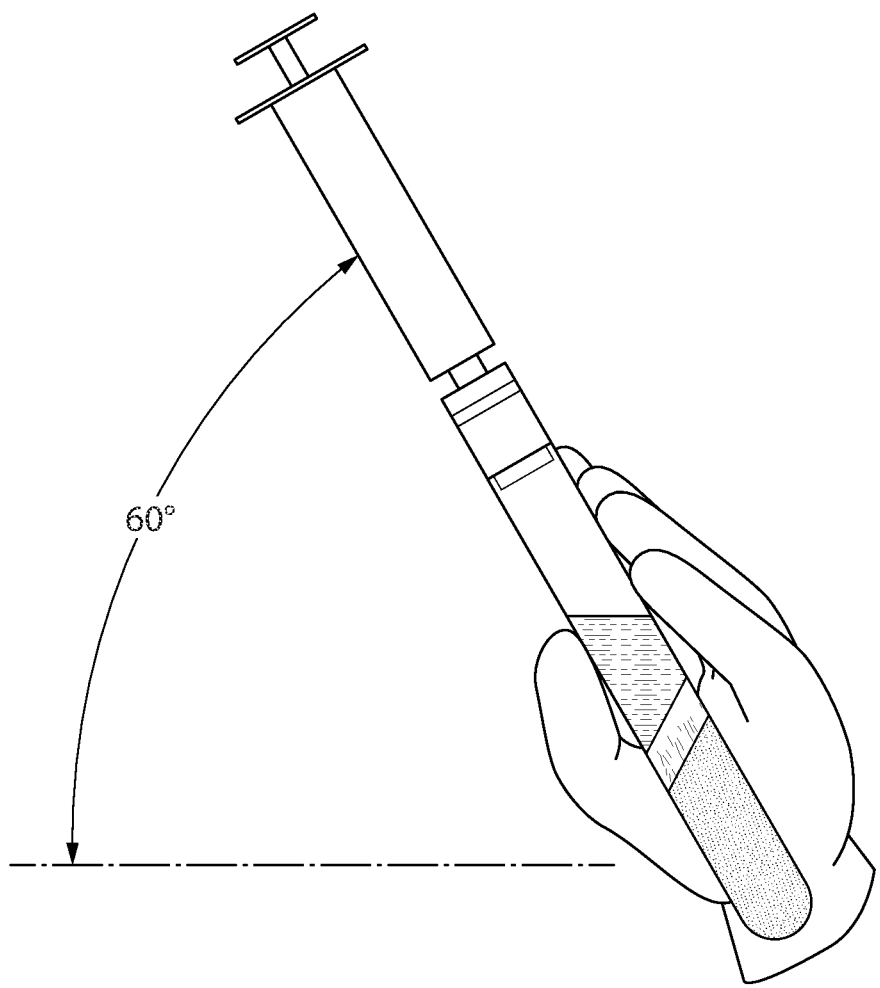
FIG. 6 depicts a third exemplary agitation angle according to certain embodiments of the present invention.

In some embodiments, the present invention provides a method for separating components of a biological sample, the method comprising: introducing a biological sample having a plurality of components to a tube comprising: a lumen; a proximal end; a distal end; an interior wall; and an exterior wall; applying a force to said tube for a time sufficient to separate said plurality of components; and agitating said tube at an angle of from about 5° to about 60°. In some embodiments, the force is a centrifugal force.

As part of the Instructions for Use (IFU), PRP systems typically call for a gentle inversion of the collection tube following centrifugation. The inversion allows for resuspension of the platelets in the sample of PRP.

In some embodiments, the present invention provides a method wherein a tube containing a separated biological sample is agitated along its long axis in a rapid manner at a rate of several times per second. In some embodiments, the method may be performed for a few seconds up to one minute. In certain embodiments, the agitation angle may be slightly negative (−15 degrees) to vertical (+90 degrees).

Without being bound by theory, the present inventors believe that the methods of the present invention create a washing (i.e., lavage of the surface of the separation barrier) that helps to release platelets that may be attached to, or adhere to the surface of the separation barrier thereby increasing the number of platelets available for resuspension and administration to a subject.

Some embodiments of the present invention provide a tube comprising a material selected from: glass; modified poly amide (MPA); polyethylene terephthalate (PET) and any other material which is inert to a biological sample. In some embodiments, the tube comprises a laminate structure wherein an exterior wall of the tube is made of a material different than the interior wall.

In some embodiments, the tube further comprises a stopper. In some embodiments, the stopper comprises a material inert to biological samples. In other embodiments, the stopper comprises a material that does not crumble. In certain embodiments, the stopper comprises butyl rubber or its halo derivative formulations. In further embodiments, the stopper has a hardness of from about forty (40) to sixty (60) Shore A. In other embodiments, the stopper has a hardness designed to provide stable vacuum for from about eighteen (18) to about twenty-four (24) months.

In some embodiments, the tube is capable of receiving biological samples of from about four (4) ml to about one hundred (100) ml. In other embodiments, the tube is designed to receive biological samples of from about eight (8) ml to about fifty (50) ml. Still further embodiments provide tubes designed to receive biological samples of from about ten (10) ml to about thirty (30) ml. Other embodiments provide tubes designed to receive biological samples of from about eleven (11) ml or about twenty-two (22) ml.

In some embodiments, the tube is selected from: a vacuum, tube, a non-vacuum tube, a plastic tube, a glass tube, a rigid tube, a non-rigid tube, a semi rigid tube and any combination thereof. In some embodiments, the terms "tube", "collection tube", "test tube", and the like, may be used interchangeably.

In some embodiments, the tube further comprises a gel. In some embodiments, the gel comprises a thixotropic gel. In further embodiments, the gel comprises a polymer. In certain embodiments, the gel can be a homopolymer or a co-polymer comprising a combination of monomers. In some embodiments, the gel comprises a polyacrylate, polyolefin or polyester.

Still further embodiments provide a gel having a density at 25° C. of from about 1.03 $g/cm^3$ to about 1.09 $g/cm^3$. While other embodiments provide a gel having a density at 25° C. of from about 1.04 $g/cm^3$ to about 1.07 $g/cm^3$. In some embodiments, the gel has a density at 25° C. of from about 1.05 $g/cm^3$.

In some embodiments, the gel has a viscosity at 30° C. of from about 1,000 to about 5,000 cps. In other embodiments, the gel has a viscosity at 30° C. of from about 1,000 to about 4,500 cps. In further embodiments, the gel has a viscosity at 30° C. of from about 1,000 to about 4,000 cps. While other embodiments utilize a gel having a viscosity at 30° C. of from about 1,000 to about 3,500 cps. Still further embodiments provide a gel having a viscosity at 30° C. of from about 1,000 to about 3,000 cps. In other embodiments, the gel has a viscosity at 30° C. of from about 1,500 to about 5,00 cps. In further embodiments, the gel has a viscosity at 30° C. of from about 2,000 to about 5,000 cps. While other embodiments utilize a gel having a viscosity at 30° C. of from about 2,500 to about 5,000 cps. Still further embodiments provide a gel having a viscosity at 30° C. of from about 3,000 to about 5,000 cps.

Yet other embodiments provide a separation barrier that does not comprise a gel, e.g. a solid float. In some embodiments, the float can take on a variety of shapes and may be constructed from a variety of materials. In certain embodiments, the float is comprised of a non-porous material and has a substantially smooth surface. In some embodiments, the separation barrier is selected from a gel; a solid float; and a combination thereof.

In some embodiments, the biological sample is autologous. In some embodiments, the biological sample comprises mammalian blood. In some embodiments, the mammalian blood comprises human blood. In some embodiments, the biological sample comprises whole blood.

Still further embodiments provide a biological sample comprising a first component comprising a plasma fraction and a second component comprising lymphocytes, monocytes and erythrocytes. In some embodiments, a centrifugal force is applied for a time sufficient to form a barrier between the first component and the second component. In other embodiments, a centrifugal force is applied for a time sufficient to form a barrier between the plasma fraction and the second component comprising lymphocytes, monocytes and erythrocytes.

In certain embodiments, the plasma fraction comprises platelets. In some embodiments, the plasma fraction comprises platelet rich plasma (PRP) and platelet poor plasma. In some embodiments, the plasma fraction comprises PRP and high-concentrated PRP. In some embodiments, the plasma fraction comprises PRP, high-concentrated PRP and ultra-high concentrated PRP.

Some embodiments further comprise the step of removing at least a portion of the first component. In some embodiments, from about twenty-five percent (25%) to about seventy-five percent (90%) of the first component is removed, optionally about thirty percent (30%) to about seventy percent (85%) of the first component is removed, about thirty-five percent (35%) to about sixty-five percent (80%) of the first component is removed, about forty percent (40%) to about sixty percent (75%) of the first component is removed, about forty-five percent (45%) to about fifty-five percent (70%) of the first component is removed, about forty-five percent (50%) to about fifty-five percent (90%) of the first component is removed, about fifty percent (50%), about sixty percent (60%), about seventy percent (70%), about eighty percent (80%), or about ninety percent (90%), of the first component is removed.

In some embodiments, the tube is agitated for a time sufficient to provide a plasma fraction having a straw color with a pinkish hue. In other embodiments, the tube is agitated for a time sufficient to provide a plasma fraction having a hue angle, h, in the CIELAB system of from 310 to 350 degrees. In further embodiments, the tube is agitated for a time sufficient to provide a plasma fraction having a hue angle, h, in the CIELAB system of from 310 to 345 degrees. In some embodiments, the tube is agitated for a time sufficient to provide a plasma fraction having a hue angle, h, in the CIELAB system of from 310 to 340 degrees. In still further embodiments, the tube is agitated for a time sufficient to provide a plasma fraction having a hue angle, h, in the CIELAB system of from 310 to 335 degrees. While in other embodiments, the tube is agitated for a time sufficient to provide a plasma fraction having a hue angle, h, in the CIELAB system of from 310 to 330 degrees. Still other embodiments provide methods wherein the tube is agitated for a time sufficient to provide a plasma fraction having a hue angle, h, in the CIELAB system of from 310 to 325 degrees. Yet other embodiments provide methods wherein the tube is agitated for a time sufficient to provide a plasma fraction having a hue angle, h, in the CIELAB system of from 310 to 320 degrees.

In some embodiments, the tube is agitated for a time sufficient to create a visually perceivable foam layer. In some embodiments, the foam layer is created on a surface of the plasma fraction. In some embodiments, the appearance of the foam layer correlates with the suspension of a clinically significant number of platelets in the plasma fraction. In other embodiments, the appearance of the foam is a signal that a clinically significant number of platelets are available for extraction and administration to a patient.

In some embodiments, the foam layer has a thickness of from about one (1) millimeter to about five (5) millimeters, optionally from about two (2) millimeters to about five (5) millimeters, or three (3) millimeters to about five (5) millimeters. While in other embodiments, the foam layer has a density of from about 0.01 $g/cm^3$ to about 0.25 $g/cm^3$, optionally from about about 0.05 $g/cm^3$ to about 0.25 $g/cm^3$, about 0.1 $g/cm^3$ to about 0.25 $g/cm^3$, about 0.15 $g/cm^3$ to about 0.25 $g/cm^3$, or about 0.2 $g/cm^3$ to about 0.25 $g/cm^3$.

In some embodiments, the tube is agitated for from about five (5) seconds to about sixty (60) seconds, optionally from about 5 seconds to about 50 seconds, about 5 seconds to about 45 seconds, about 5 seconds to about 40 seconds, about 5 seconds to about 35 seconds, about 5 seconds to about 30 seconds, about 5 seconds to about 25 seconds, about 5 seconds to about 20 seconds, about 5 seconds to about 15 seconds, or about 5 seconds to about 10 seconds.

In some embodiments, the agitation is stepwise. In some embodiments, the stepwise agitation comprises a plurality of five second intervals of agitation. In other embodiments, the stepwise agitation further comprises a break between five second intervals. In certain embodiments, the break is from about 0.1 seconds to about 5 seconds.

In some embodiments, the agitation is a rhythmic motion. In some embodiments, the agitation creates a longitudinal or transverse wave-like motion in the biological sample. In some embodiments, the agitation creates a mixed longitudinal and transverse wave-like motion in the biological sample.

In some embodiments, a centrifugal force of from about 500 g to about 5000 g is applied to said tube. In other embodiments, a centrifugal force of from about 750 g to about 5000 g is applied to said tube. While in other embodiments, a centrifugal force of from about 1000 g to about 5000 g is applied to said tube. In yet other embodiments, a centrifugal force of from about 1500 g to about 5000 g is applied to said tube. In some embodiments, a centrifugal force of from about 2000 g to about 5000 g is applied to said tube. In some embodiments, a centrifugal force of from about 2500 g to about 5000 g is applied to said tube. In some embodiments, a centrifugal force of from about 3000 g to about 5000 g is applied to said tube. In other embodiments, a centrifugal force of from about 3000 g to about 4000 g is applied to said tube. While in other embodiments, a centrifugal force of from about 1500 g to about 2500 g is applied to said tube.

In some embodiments, the centrifugal force creates a plasma-gel interface between a surface of the gel and a surface of the plasma fraction. In some embodiments, the plasma-gel interface comprises platelets. In certain embodiments, the platelets in the plasma-gel interface are releasably bound to a surface of the gel. In some embodiments, the agitation releases platelets from the plasma-gel interface. In some embodiments, the platelets released from the plasma-gel interface are suspended in the plasma fraction.

In some embodiments, the tube further comprises (or contains) an anticoagulant. In some embodiments, the anticoagulant is selected from: a citrate salt (e.g. buffered sodium citrate); an EDTA salt (potassium-ethylenediaminetetra-acid); citrate-theophylline-adenosine-dipyridamole (CTAD); hirudin, benzylsulfonyl-d-Arg-Pro-4-amidinobenzylamide (BAPA); citric/citrate dextrose (ACD); heparin; an iodo acetate salt; an oxalate salt; a fluoride salt; and a combination of two or more thereof. Certain embodiments of the present invention do involve the use of a tube comprising an anticoagulant. In such embodiments, the biological sample may have been pre-treated with anticoagulant or the biological sample does not need to be anticoagulated.

Other embodiments provide compositions comprising a product of any one of the methods or systems described herein. Still further embodiments provide for the use of a composition comprising a product of any one of the methods or systems described herein for treating or preventing alopecia, bed sores, wrinkles, pain, tendonitis, arthritis, acne, scarring, crow's feet, ligament sprains and tears, and/or skin lesions.

Still further embodiments provide systems for separating components of a biological sample comprising: a biological sample; a tube; a means for applying a centrifugal force to said tube (e.g. a centrifuge); and a means for agitating said tube. In some embodiments, the systems described herein further comprise a means for measuring color in a biological sample. In some embodiments, the means for measuring color in a biological sample is selected from a spectrophotometer and a densitometer.

In some embodiments, the centrifuge is selected from a fixed angle centrifuge and horizontal spin centrifuge, or a swinging bucket centrifuge.

In some embodiments, the means for agitating the tube is adapted to linearly agitate the tube. In some embodiments, the means for agitating the tube is a tube rocker.

Some embodiments of the present invention provide a system as described herein further comprising a platelet counter. While other embodiments further comprise a processor. In some embodiments, the processor is wirelessly coupled to the means for applying a centrifugal force; the means for agitating the tube; the means for measuring color in a biological sample; and the platelet counter. In some embodiments, the means for applying a centrifugal force; the means for agitating the tube; the means for measuring color in a biological sample; the platelet counter; and the processor are contained in a single apparatus.

As used herein, the term "available platelet count" (or "APC") is intended to refer to the number of platelets that are readily accessible to the clinician for administration to a subject in need thereof.

In some embodiments, the methods and systems described herein increase the available platelet count ("APC") by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 200%, about 250%, about 300%, about 400%, or about 500%, versus the platelet count provided by a control system. In some embodiments, the control system substantially similar system those encompassed by the present invention, except for the absence of a means for agitating the tube; and/or a substantially similar system wherein the means for agitating the tube is only able to agitate the tube at an angle less than 5°, or at an angle greater than 60°.

In some embodiments, the means for agitating the tube is adapted to agitate the tube at an angle of from about 5° to about 60°, about 5° to about 55°, about 5° to about 50°, about 5° to about 45°, about 5° to about 40°, about 5° to about 35°, about 5° to about 30°, about 5° to about 25°, about 5° to about 20°, about 5°, about 10°, about 15°, about 20°, about 25°, about 30°, about 35°, about 40°, about 45°, about 50°, about 55°, or about 60°. As used herein, "agitation angle" and the like are intended to refer to the angle measured from horizontal.

In some embodiments, the methods and systems described herein provide an available platelet count ("APC") of greater than about 375,000 platelets/microliter, about 400,000 platelets/microliter, about 425,000 platelets/microliter, about 450,000 platelets/microliter, about 475,000 platelets/microliter, about 500,000 platelets/microliter, about 525,000 platelets/microliter, about 550,000 platelets/microliter, about 575,000 platelets/microliter, about 600,000 platelets/microliter, about 625,000 platelets/microliter, about 650,000 platelets/microliter, about 675,000 platelets/microliter, about 700,000 platelets/microliter, about 725,000 platelets/microliter, about 750,000 platelets/microliter, about 775,000 platelets/microliter, about 800,000 platelets/microliter, about 825,000 platelets/microliter, about 850,000 platelets/microliter, about 875,000 platelets/microliter, about 900,000 platelets/microliter, about 925,000 platelets/microliter, about 950,000 platelets/microliter, or about 975,000 platelets/microliter.

Other embodiments provide methods for: suspending platelets in a post-centrifuged biological sample; increasing APC in a biological sample; and/or enriching the platelet count in a biological sample, comprising: centrifuging a collection tube containing a biological sample and a thixotropic gel; and agitating the collection tube at an angle and rate effective to create a layer of foam on top of said biological sample.

For avoidance of doubt, at least a portion of any one of the methods described herein could be suitable for use in any one of the systems described herein.

Referring first to FIG. 1, an exemplary tube (100) containing a biological sample post-centrifugation is depicted. As shown therein, the plasma fraction (110) comprises platelet poor plasma (120) and platelet rich plasma (130), wherein the platelet rich plasma (130) has a portion of ultra-high platelet concentration, sometimes referred to as ultra-high platelet rich plasma (140). Also depicted in FIG. 1 is the plasma-gel interface (150).

FIGS. 2-6 depict three exemplary agitation angles of the present invention and two comparative agitation angles. As discussed herein, the agitation angle is measured from the horizontal plane.

Figure 7:
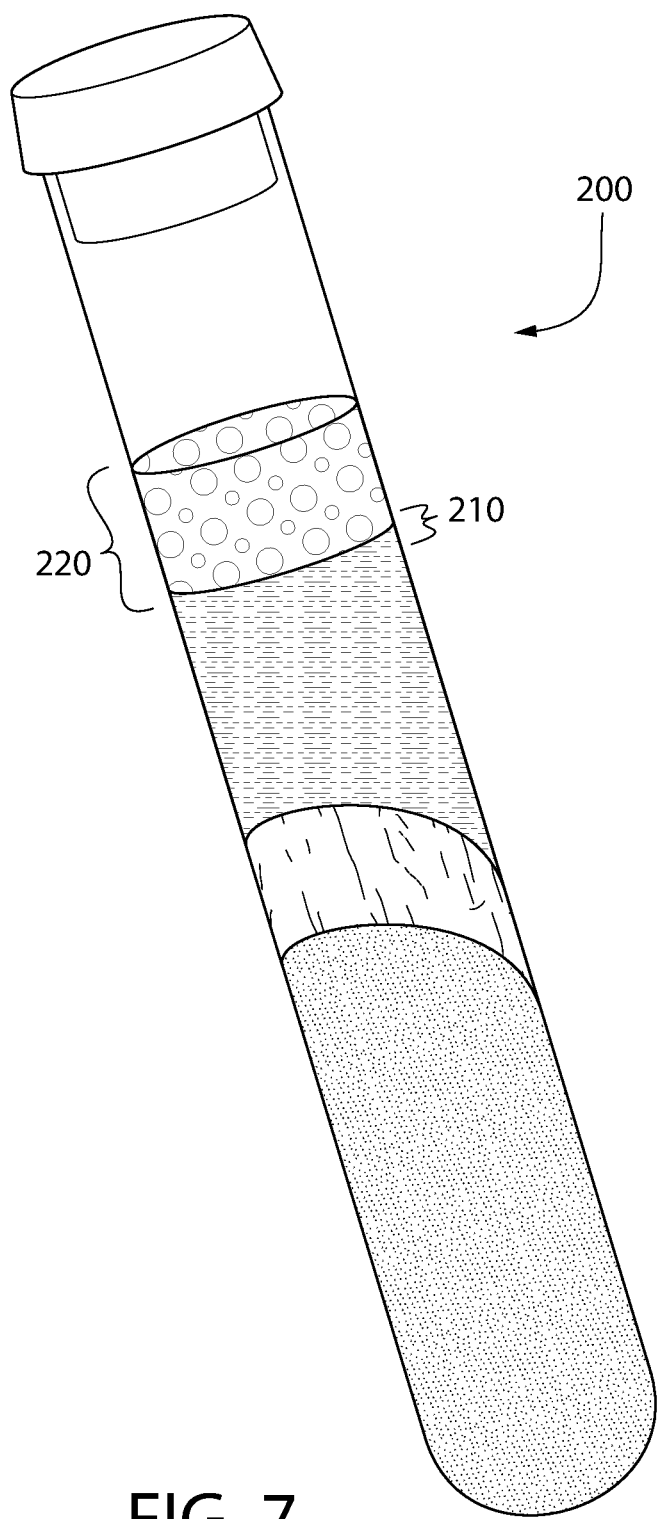
FIG. 7 illustrates the foam created by an exemplary embodiment of the present invention.
Figure 8:
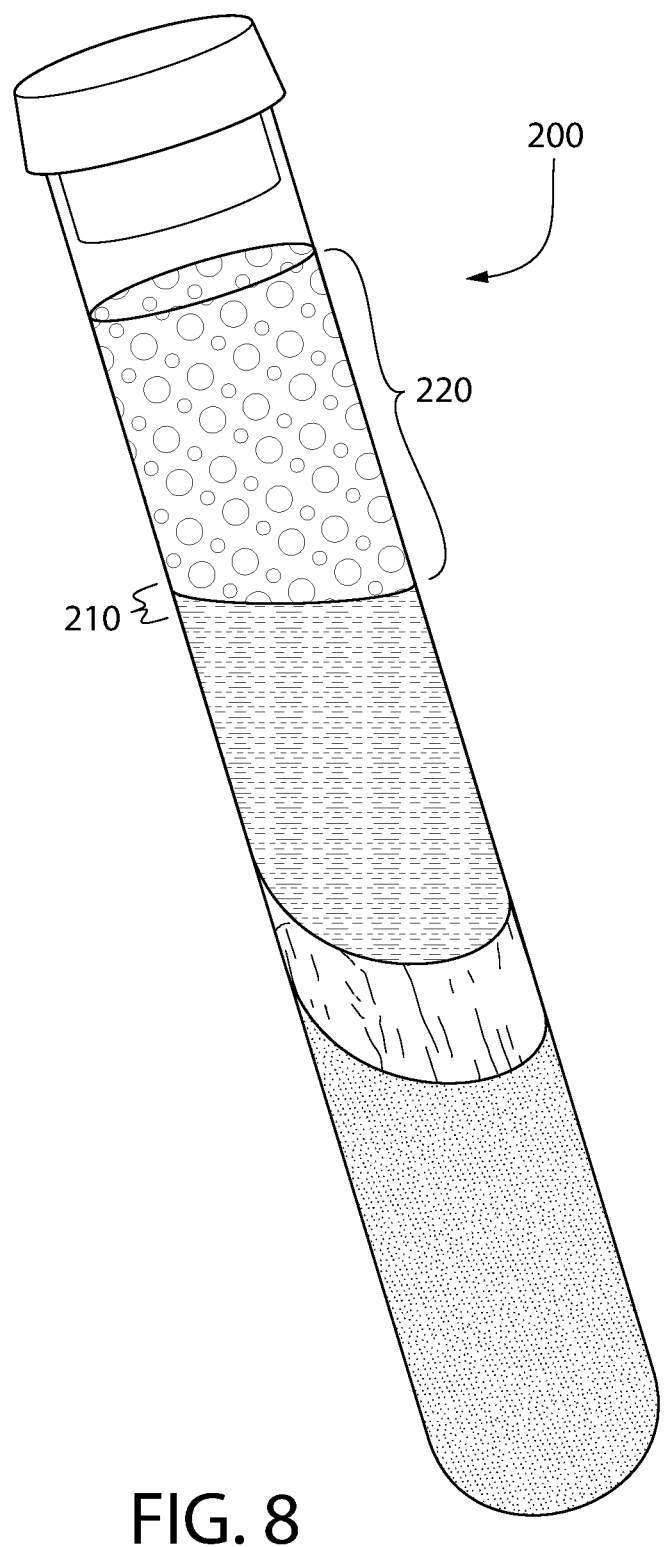
FIG. 8 illustrates the foam created by another exemplary embodiment of the present invention.

Referring next to FIGS. 7-8, a tube (200) containing a biological sample after centrifugation and agitation in accordance with certain embodiments of the present invention is depicted. FIGS. 7 and 8 also depict the layer of foam (220) that appears on the top surface of the plasma fraction (210).

Figure 9:
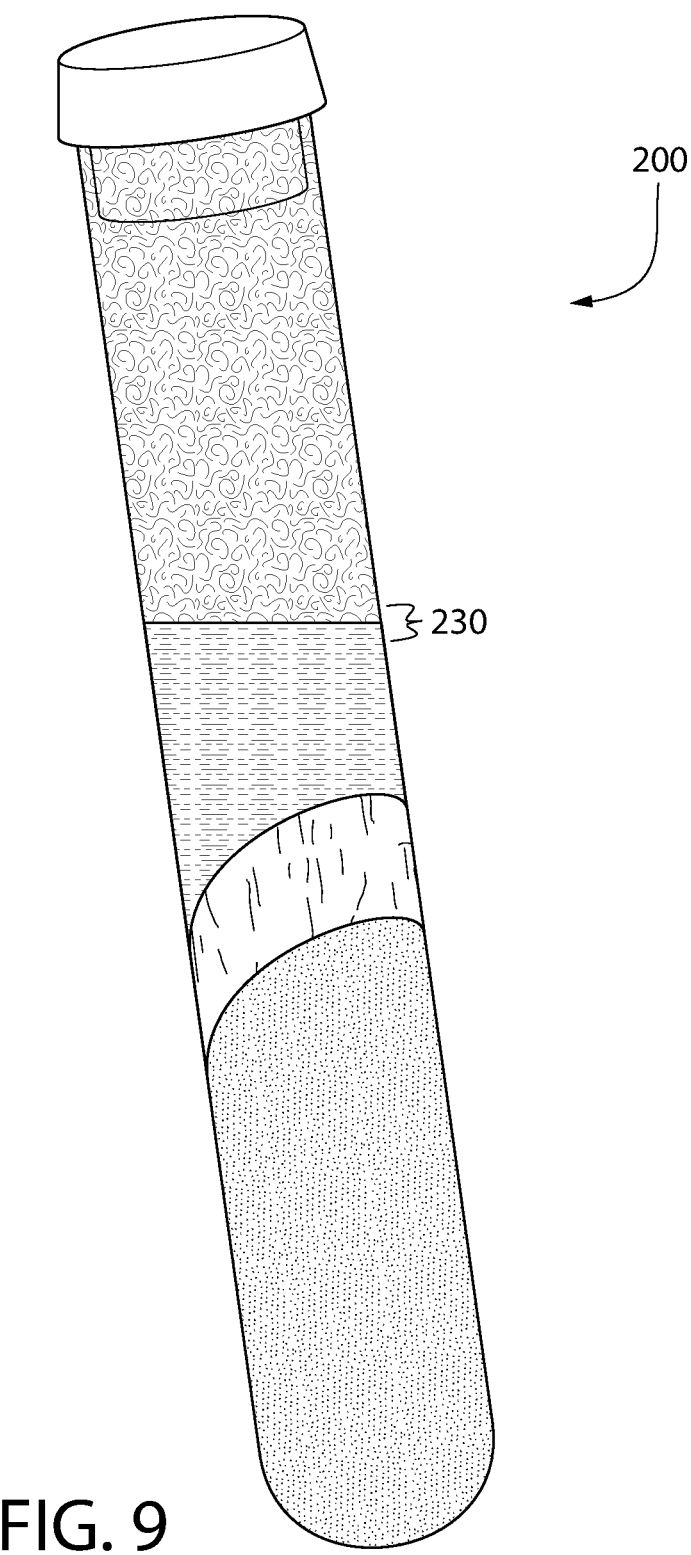
FIG. 9 illustrates the absence of foam when a comparative method is performed.

In contrast to FIGS. 7 and 8, tube (200) of FIG. 9 does not include a layer of foam on the top surface of the plasma fraction (230).

Further areas of applicability of the present invention will become apparent from the detailed description provided hereinafter. It should be understood that the detailed description and specific examples, while describing exemplary embodiments, are intended for purposes of illustration only and are not intended to limit the scope of the present invention.

EXAMPLES

Example 1

A series of experiments were conducted to compare exemplary methods of the present invention to current methods of preparing PRP; and to understand how certain features impact platelet suspension and capture. In particular, agitation angle, agitation time, color of the biological sample and the presence of foam were evaluated. Change in color and the presence of foam were evaluated at various time points during the experiments. As described in Table 1 (below), experiments conducted with exemplary agitation angles and agitation times of the present invention provided surprisingly increased platelet counts with minimal to no infiltration of unwanted cells from the biological sample (e.g. erythrocytes). The results of these experiments are described in Table 1 (below).

TABLE 1

| Method | Agitation Angle (°) | Agitation Time (seconds) | Color | Platelet Count (100K/μl) |
|---|---|---|---|---|
| Whole Blood | n/a | n/a | Deep red | 193 |
| Comp. Ex. 1* | n/a | n/a | Straw | 355 |
| Comp. Ex. 2 | 15 | 60 | Deep red | n/a |
| Comp Ex. 3 | 45 | 10 | Straw | 397 |
| Ex. 1 | 15 | 10 | Straw w/pink hue | 505 |
| Ex. 2 | 15 | 30 | Straw w/rose hue | 436 |
| Ex. 3 | 45 | 5 | Straw w/pink hue | 416 |
| Ex. 4 | 45 | 30 | Straw w/rose hue | 415 |
| Ex. 5 | 45 | 60 | Light rose | 480 |

Comp. Ex. 1 was a method performed in accordance with techniques known in the industry, wherein the tube was gently inverted horizontally twenty times.

As illustrated by the data described in Table 1 (above) the exemplary methods of the present invention surprisingly increased platelet counts with acceptable levels of infiltrate. A foam layer was also observed with each of the exemplary methods of the present invention. Without being bound by theory, the present inventors believe that agitation angle, agitation time and agitation rate are critical to achieving clinically maximal platelet counts. In addition, the appearance of foam on top of the plasma fraction provides a signal to the clinician that the desired platelet concentration has been achieved, as it correlates with the increased platelet counts.

Example 2

Additional experiments were conducted to further demonstrate the increased platelet counts provided by exemplary methods of the present invention. Five (5) samples from different donors were studied to evaluate the effect of the inventive methods at discrete time intervals ranging from five (5) seconds to one (1) minute. The impact of various agitation angles, ranging from −15° to 90° from horizontal, were also evaluated. The impact of both fixed angle and swing-bucket centrifuges was also evaluated. Platelet counts were performed using an automated Horiba ABX Micros 60 Hematology Analyzer (Horiba Instruments, Inc., Irvine Calif.).

The results of these experiments are described below in Tables 2 to 6. In each experiment 3 mL of platelet poor plasma (PPP) was removed before the platelets were counted in the PRP sample.

WB=Whole Blood

IFU=Instructions for Use

IFU platelet counts refer to platelet counts obtained using techniques known in the industry, wherein the tube was gently inverted horizontally twenty times.

TABLE 2

| | | | \multicolumn{8}{c}{WB Platelet Count = 202/IFU Platelet Count = 241} |
| | Setting | | Agitation Time (Seconds) | | | | | | | |
| Centrifuge | (speed × time) | Angle | 5 | 10 | 15 | 20 | 30 | 40 | 50 | 60 |
|---|---|---|---|---|---|---|---|---|---|---|
| Fixed | 3300 × 10 | −15 | 270 | 391 | 432 | 478 | 469 | n/a | — | — |
| Fixed | 3300 × 10 | 0 | 281 | 402 | 460 | 572 | 564 | 596 | 577 | — |
| Fixed | 3300 × 10 | 15 | 300 | 376 | 442 | 520 | 563 | 626 | 607 | — |
| Fixed | 3300 × 10 | 45 | 266 | 358 | 302 | 371 | n/a | — | — | — |
| Fixed | 3300 × 10 | 90 | 305 | 398 | n/a | — | — | — | — | — |

TABLE 3

| | | | \multicolumn{8}{c}{WB Patelet Count = 335/IFU Platelet Count = 437} |
| | Setting | | Agitation Time (Seconds) | | | | | | | |
| Centrifuge | (speed × time) | Angle | 5 | 10 | 15 | 20 | 30 | 40 | 50 | 60 |
|---|---|---|---|---|---|---|---|---|---|---|
| Fixed | 3300 × 10 | −15 | 442 | 461 | 438 | 425 | n/a | — | — | — |
| Fixed | 3300 × 10 | 0 | 498 | 529 | 571 | 602 | 639 | n/a | — | — |
| Fixed | 3300 × 10 | 15 | 501 | 535 | 581 | 672 | 602 | 628 | 638 | 649 |
| Fixed | 3300 × 10 | 45 | 471 | 495 | 502 | 462 | n/a | — | — | — |
| Fixed | 3300 × 10 | 90 | 521 | n/a | — | — | — | — | — | — |

TABLE 4

| | | | \multicolumn{8}{c}{WB Platelet Count = 263/IFU Platelet Count = 358} |
| | Setting | | Agitation Time (Seconds) | | | | | | | |
| Centrifuge | (speed × time) | Angle | 5 | 10 | 15 | 20 | 30 | 40 | 50 | 60 |
|---|---|---|---|---|---|---|---|---|---|---|
| Fixed | 3300 × 10 | −15 | 379 | 401 | n/a | — | — | — | — | — |
| Fixed | 3300 × 10 | 0 | 421 | 482 | 508 | 637 | 605 | n/a | — | — |
| Fixed | 3300 × 10 | 15 | 439 | 521 | 595 | 639 | 678 | 654 | 638 | — |
| Fixed | 3300 × 10 | 45 | 444 | 507 | 582 | 604 | n/a | — | — | — |
| Fixed | 3300 × 10 | 90 | 402 | n/a | — | — | — | — | — | — |

TABLE 5

| | | | \multicolumn{8}{c}{WB Platelet Count = 321/IFU Platelet Count = 447} |
| | Setting | | Agitation Time (Seconds) | | | | | | | |
| Centrifuge | (speed × time) | Angle | 5 | 10 | 15 | 20 | 30 | 40 | 50 | 60 |
|---|---|---|---|---|---|---|---|---|---|---|
| Swing | 3300 × 10 | −15 | 487 | 521 | 591 | 667 | 582 | — | — | — |
| Swing | 3300 × 10 | 0 | 598 | 671 | 778 | 864 | 701 | 728 | — | — |
| Swing | 3300 × 10 | 15 | 608 | 788 | 901 | 853 | 846 | — | — | — |
| Swing | 3300 × 10 | 45 | 570 | 605 | 739 | 704 | 698 | — | — | — |
| Swing | 3300 × 10 | 90 | 683 | 721 | 629 | — | — | — | — | — |

TABLE 6

| | | | \multicolumn{8}{c}{WB Platelet Count = 172/IFU Platelet Count = 304} |
| | Setting | | Agitation Time (Seconds) | | | | | | | |
| Centrifuge | (speed × time) | Angle | 5 | 10 | 15 | 20 | 30 | 40 | 50 | 60 |
|---|---|---|---|---|---|---|---|---|---|---|
| Swing | 3300 × 10 | −15 | 387 | 419 | 601 | 662 | 583 | 539 | — | — |
| Swing | 3300 × 10 | 0 | 408 | 488 | 573 | 701 | 745 | 705 | 728 | — |
| Swing | 3300 × 10 | 15 | 584 | 707 | 853 | 690 | 707 | — | — | — |

TABLE 6-continued

| | | WB Platelet Count = 172/IFU Platelet Count = 304 | | | | | | | | |
|---|---|---|---|---|---|---|---|---|---|---|
| | Setting | | Agitation Time (Seconds) | | | | | | | |
| Centrifuge | (speed × time) | Angle | 5 | 10 | 15 | 20 | 30 | 40 | 50 | 60 |
| Swing | 3300 × 10 | 45 | 551 | 674 | 779 | 871 | 720 | — | — | — |
| Swing | 3300 × 10 | 90 | 402 | 336 | — | — | — | — | — | — |

As illustrated by the data described in Tables 2 to 6 (above), exemplary methods of the present invention produce unexpected increases in platelet counts when compared to the platelet counts produced by conventional methods. These differences are not only numerically significant, but they also provide a clinically significant advance to the state of the art. Although the optimal time and angle may vary, the data unequivocally show that the agitation method, across the range of times and angles studied, increased platelet counts, thereby increasing the therapeutic dose of platelets that can be delivered to a subject.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for:
    suspending platelets in a post-centrifuged biological sample;
    increasing the number of platelets available for administration to a patient; and/or
    enriching the platelet count in a biological sample,
comprising:
    centrifuging a collection tube containing a biological sample and a separation barrier;
    maintaining the collection tube at an angle of from about −15° to about 90°; and
    agitating the collection tube at said angle and at a rate effective to create a thin layer of foam on top of said biological sample.

2. The method according to claim 1, wherein the collection tube further comprises an anticoagulant.

3. The method according to claim 2, wherein the anticoagulant is selected from: a citrate salt; an ethylenediaminetetraacetic acid (EDTA) salt; citrate-theophylline-adenosine-dipyridamole (CTAD); hirudin, benzylsulfonyl-d-Arg-Pro-4-amidinobenzylamide (BAPA); citric/citrate dextrose (ACD); heparin; an iodo acetate salt; an oxalate salt; a fluoride salt; and a combination of two or more thereof.

4. The method according to claim 1, wherein the biological sample comprises a plurality of components.

5. The method according to claim 4, wherein the centrifugation is performed at a force of from about 500 g up to about 4000 g for a time sufficient to separate the plurality of components in the biological sample.

6. The method according to claim 5, wherein the separation barrier forms a barrier between the plurality of components of the biological sample.

7. The method according to claim 1, wherein the biological sample comprises whole blood.

8. The method according to claim 1, wherein the biological sample comprises a first component comprising a plasma fraction; and a second component comprising lymphocytes, monocytes and erythrocytes.

9. The method according to claim 8, wherein the plasma fraction comprises platelets.

10. The method according to claim 9, wherein the plasma fraction comprises platelet rich plasma and platelet poor plasma.

11. The method according to claim 10, further comprising the step of removing at least a portion of the first component.

12. The method according to claim 8, wherein the foam layer is created on a surface of the plasma fraction.

13. The method according to claim 8, wherein the separation barrier comprises a gel.

14. The method according to claim 13, wherein a centrifugal force creates a plasma-gel interface between a surface of the gel and a surface of the plasma fraction.

15. The method according to claim 14, wherein the plasma-gel interface comprises platelets.

16. The method according to claim 15, wherein the platelets in the plasma-gel interface are releasably bound to the gel surface.

17. The method according to claim 16, wherein the agitation releases platelets from the plasma-gel interface.

18. The method according to claim 17, wherein the platelets released from the plasma-gel interface are suspended in the plasma fraction.

19. The method according to claim 1, wherein the collection tube is agitated for from about one (1) second to about sixty (60) seconds, optionally from about four (4) seconds to about forty (40) seconds, about five (5) seconds to about sixty (60) seconds, about 5 seconds to about 50 seconds, about 5 seconds to about 45 seconds, about 5 seconds to about 40 seconds, about 5 seconds to about 35 seconds, about 5 seconds to about 30 seconds, about 10 seconds to 30 seconds, about 10 seconds to about 20 seconds, about 5 seconds to about 25 seconds, about 5 seconds to about 20 seconds, about 5 seconds to about 15 seconds, or about 5 seconds to about 10 seconds.

20. The method according to claim 1, wherein the collection tube is agitated for a time sufficient to provide a plasma fraction having a hue angle, h, in the CIELAB system of from 310 to 350 degrees.

21. The method according to claim 1, wherein the method increases the available platelet count (APC) by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 200%, about 250%, about 300%, about 400%, or about 500%, versus the platelet count provided by a control system.

22. The method according to claim 1, wherein the foam layer has a density of from about 0.01 g/cm³ to about 0.25 g/cm³.

23. The method according to claim 1, wherein the collection tube is maintained at an angle of from about 0° to about 90°.

24. The method according to claim 1, wherein the collection tube is maintained at an angle of from about 5° to about 60°.

25. The method according to claim 1, wherein the collection tube is maintained at an angle of from about 15° to about 45°.

* * * * *